United States Patent [19]
Schreiber

[11] Patent Number: 5,449,360
[45] Date of Patent: * Sep. 12, 1995

[54] OSTEOTOMY DEVICE AND METHOD

[76] Inventor: Saul N. Schreiber, 6525 N. Central Ave., Phoenix, Ariz. 85012

[ * ] Notice: The portion of the term of this patent subsequent to Jan. 7, 2009 has been disclaimed.

[21] Appl. No.: 23,585

[22] Filed: Feb. 26, 1993

Related U.S. Application Data

[63] Continuation-in-part of Ser. No. 749,278, Aug. 23, 1991, Pat. No. 5,246,444.

[51] Int. Cl.⁶ .............................................. A61F 5/00
[52] U.S. Cl. ........................................ 606/87; 606/96
[58] Field of Search .................................. 606/86–90, 606/96–98, 104, 105, 79

[56]  References Cited

U.S. PATENT DOCUMENTS

| | | | |
|---|---|---|---|
| 4,335,715 | 6/1982 | Kirkley | 606/87 |
| 4,349,018 | 9/1982 | Chambers | 606/88 |
| 4,421,112 | 12/1983 | Mains et al. | 606/88 |
| 4,750,481 | 6/1988 | Reese | 606/87 |
| 4,952,214 | 8/1990 | Comparetto | 606/87 |
| 5,053,039 | 10/1991 | Hofmann et al. | 606/87 |
| 5,078,719 | 1/1992 | Schreiber | 606/87 |

Primary Examiner—Peter A. Aschenbrenner
Attorney, Agent, or Firm—Harry M. Weiss

[57]  ABSTRACT

This invention relates to a device and method therefor used in osteotomy for removing a right-angled bone wedge from a leg bone. The device consists of a trapezoidal block with a detachable connecting member which is used with detachable towers and surgical pins that allows the surgeon to establish a reference external to the bone as to the position of the apex and angle of the wedge to be cut and then to drill the surgical pins into the leg bone to secure the block in position. The block includes integral saw guides having interconnected upper and lower guide slots to translate the reference into the bone as saw cuts which precisely remove the required wedge of bone. The connecting member is then detached and the block and pins removed to allow completion of the surgical procedure.

14 Claims, 8 Drawing Sheets

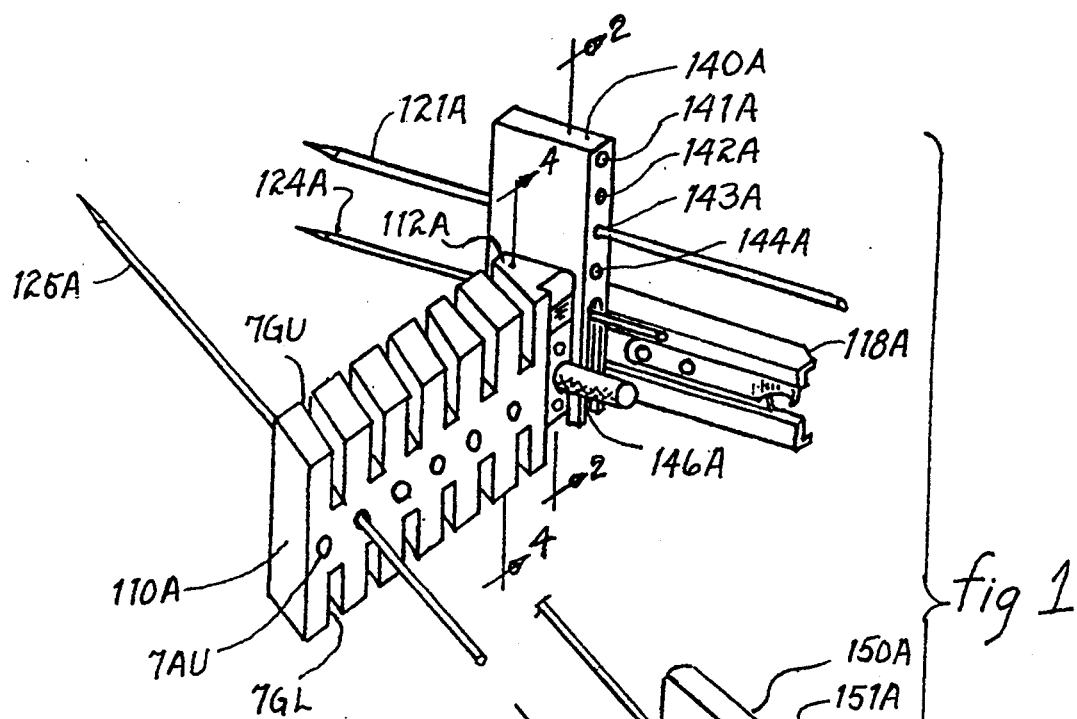
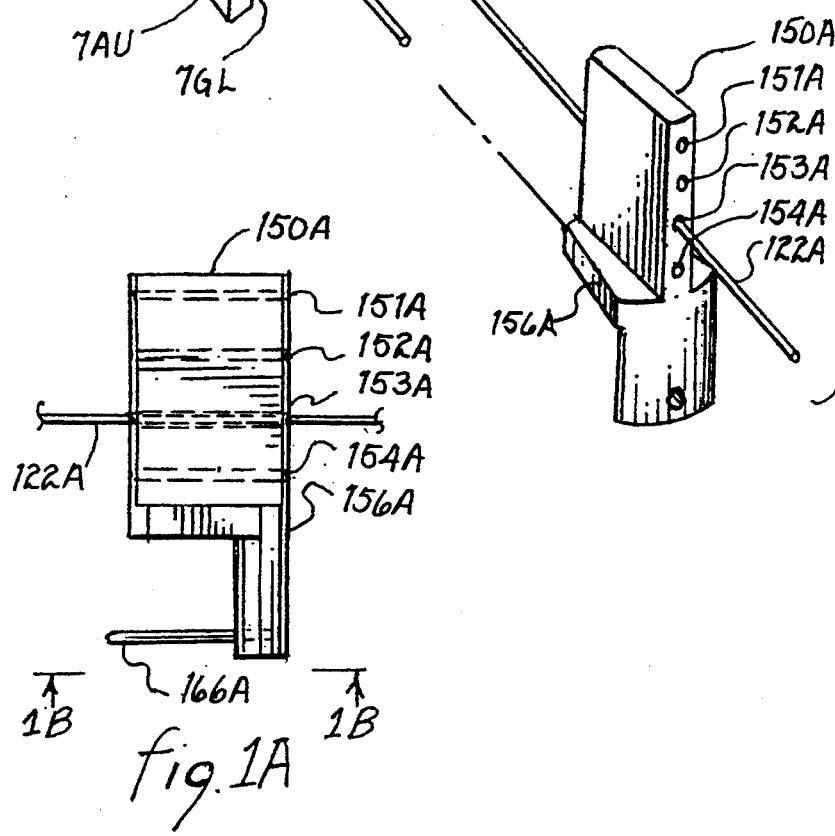
fig. 1A
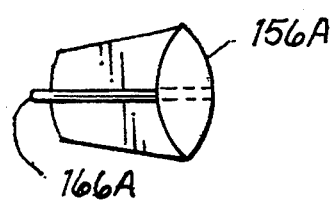
fig. 1B

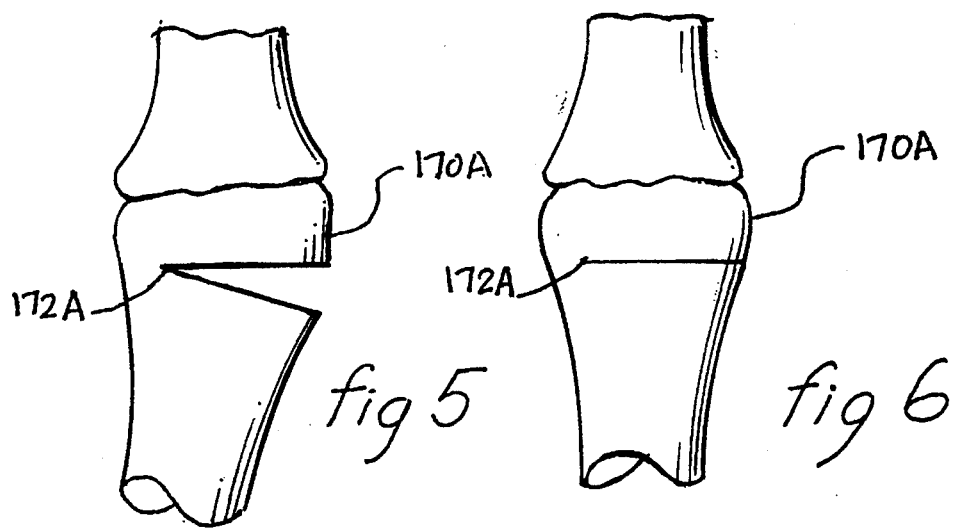
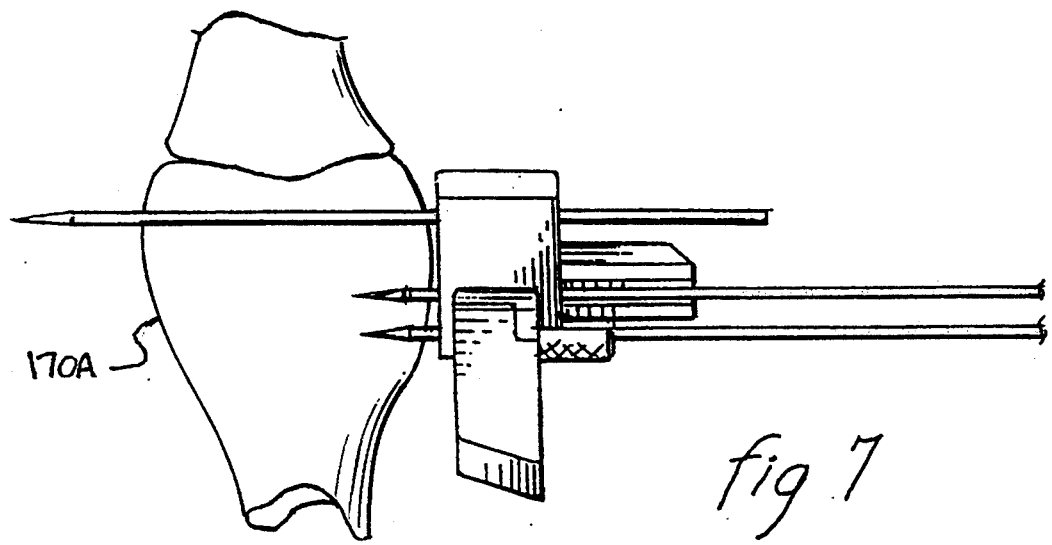

OSTEOTOMY DEVICE AND METHOD

This patent application is a continuation-in-part of Ser. No. 07/749,278, filed Aug. 23, 1991, now U.S. Pat. No. 5,246,444 entitled Osteotomy Device and Method Therefore.

BACKGROUND OF THE INVENTION

1. Field of Invention

This invention relates generally to an osteotomy device and methods for its use. More particularly, this invention relates to an osteotomy device and method in which a rigid block is positioned in alignment with a patient's leg bone and saw guides incorporated in this block and arranged to be accessible from above or below this block are used for precisely locating two intersecting bone cuts below a person's knee portion so that a bone wedge can be removed to correct for leg deformities such as for bowleggedness.

2. Background of the Invention

Osteotomy is a surgical procedure which involves cutting and removing a section of bone. The procedure is used to correct many types of bone deformities found in the human leg. For example, in the instance of improper leg formation during growth, undesired angulation or orientation of a particular bone with respect to other bones of the leg often occurs such as the condition referred to as bowleggedness The surgical procedure for overcoming this type of medical problem normally involves the removal of a wedge-shaped section of the knee portion of the malformed or misaligned leg at a predetermined location which causes the relative repositioning of the remaining bone sections of the leg so as to impart to the surgically corrected leg the proper relative configuration or orientation. The wedge-shaped section removed from the original knee bone is, of course, of a predetermined size which naturally depends upon extent of the correction required. For example, by known techniques, an orthopedic surgeon can determine the extent of leg deformity and the required amount of a wedge that is needed to correct the leg deformity.

To make the correct adjustment to the leg requires not only cutting out the correctly sized bone wedge portion at a proper angle, but also assuring that there remains, at the apex of the wedge, residual bone of sufficient thickness to prevent a complete severance or fracture of the bone and to promote mending together of the cut or bone portions. Also, to ensure correct realignment of the bone, it is essential that the cuts into the bone, performed to remove the wedge-shaped segment, be substantially smooth and planar so that, when the severed end regions of portions of the remaining bone segments are brought into contact their surfaces mate uniformly across the entire severed surfaces to promote rapid and structurally effective mending of the cut bone portion. Furthermore, to assure this rapid mending, often times a suitably shaped blade plate or side plate is coupled, by screws, to the remaining bone segments, after removal of the wedge portion, and is used to hold the segments together. To properly use such a blade plate this requires that the removed wedge portion have a right angle configuration.

U.S. Pat. No. 4,335,715 issued Jun. 22, 1982 to W. H. Kirkley or "Osteotomy Guide" discloses an apparatus in which a pair of pins positioned on an arcuate track are inserted into the bone to serve as a guide for the surgeon in making cuts into the bone. The device has no means for determining the apex of the wedge. Therefore, the surgeon must rely on his judgment to determine the apex or remove an entire wedge without leaving any residual bone. Obviously, such a procedure complicates the healing process.

U.S. Pat. No. 4,349,018, issued Sep. 14, 1982 to G. R. Chambers for "Osteotomy Apparatus" discloses a fairly complex and cumbersome device for guiding saw cuts in a operation for the total removal of the Knee. Because of the device's complexity it is ill suited for simpler osteotomy procedures.

U. S. Pat. No. 4,627,425, issued Dec. 9, 1986 to H. W. Reese for "Osteotomy Appliances and Method" discloses a guide to be used by the surgeon to make a second cut in a bone at a predetermined angle from a first cut. To locate the apex of the wedge, a pin has to be inserted vertically into the bone. Also, the device produces a wedge without a right angle and therefore cannot be used with the blade plate or side plate described above.

U.S. Pat. No. 4,757,810, issued Jul. 19, 1988 to H. W. Reese for "Osteotomy Apparatus and Method" discloses a guide for precisely locating two parallel, spaced apart bone cuts. This guide however cannot be used to cut a wedge from the bone.

Still there is a need for a osteotomy device that would allow a surgeon to remove a pre-calculated sized bone wedge having a right angle, that would leave a sufficient amount of residual bone, that does not require drilling a vertical pin into the bone to locate the apex of the wedge and that provides a integral saw guide that would allow access to different aspects of the bone to thereby simplify the sawing of the bone wedge.

SUMMARY OF THE INVENTION

An object of the present invention is to provide an osteotomy device with integral saw guide and method therefor for removing a bone wedge having a right angle.

Another object of the present invention is to provide an osteotomy device with integral saw guide and method therefor that can locate the apex of a bone wedge to be removed without drilling a pin vertically into the bone.

Yet another object of the present invention is to provide an osteotomy device with integral saw guide and method therefor that would enable the surgeon to leave a sufficient amount of residual bone after making the cuts into the bone (for example of a wedge of bone) so as to inhibit the fracturing of the bone.

Yet another object of the present invention is to provide an osteotomy device with integral saw guide and method therefor that would enable the surgeon to make a guided saw cut from different aspects with respect to the bone, for example from above and below the bone.

The subject invention accomplishes these objects by providing a device and method therefor that allows the surgeon to establish a reference external to the bone as to the position of the apex and angle of the wedge to be cut and then to make use of an integral saw guide having interconnected upper and lower guide slots to translate those references into the bone as saw cuts which precisely remove the required wedge of bone.

These and other objects, features and advantages of the present invention, as well as details of the preferred embodiment thereof, will be more fully understood from the following description and drawing.

BRIEF DESCRIPTION OF THE DRAWINGS

FIG. 1 is a perspective view of the osteotomy device of this invention.

FIG. 1A is a cross-sectional view of tower 150A of FIG. 1.

FIG. 1B is a bottom view of tower 150A of FIG. 1 taken along line 1B—1B.

FIG. 5 is a vertical side view of a model of a leg bone with a bone wedge removed before straightening out the bottom leg portion.

FIG. 6 is a vertical side view of the same leg model reoriented after the bone wedge has been removed showing the bottom leg portion straightened out with respect to the knee portion.

FIG. 7 is a perspective view of the osteotomy device positioned next to the model of the leg bone after insertion of a first (top pin) therein.

DESCRIPTION OF THE PREFERRED EMBODIMENT

Figure 4:
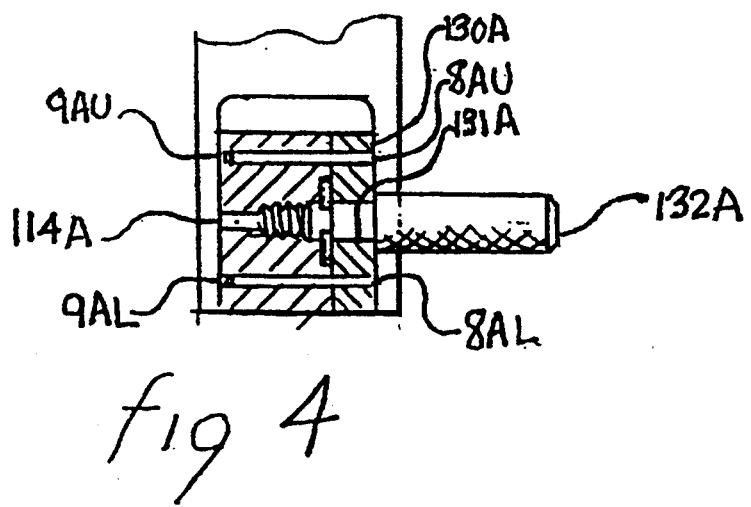
FIG. 4 is a cross-sectional view taken along line 4—4 of FIG. 1.
Figure 3A:
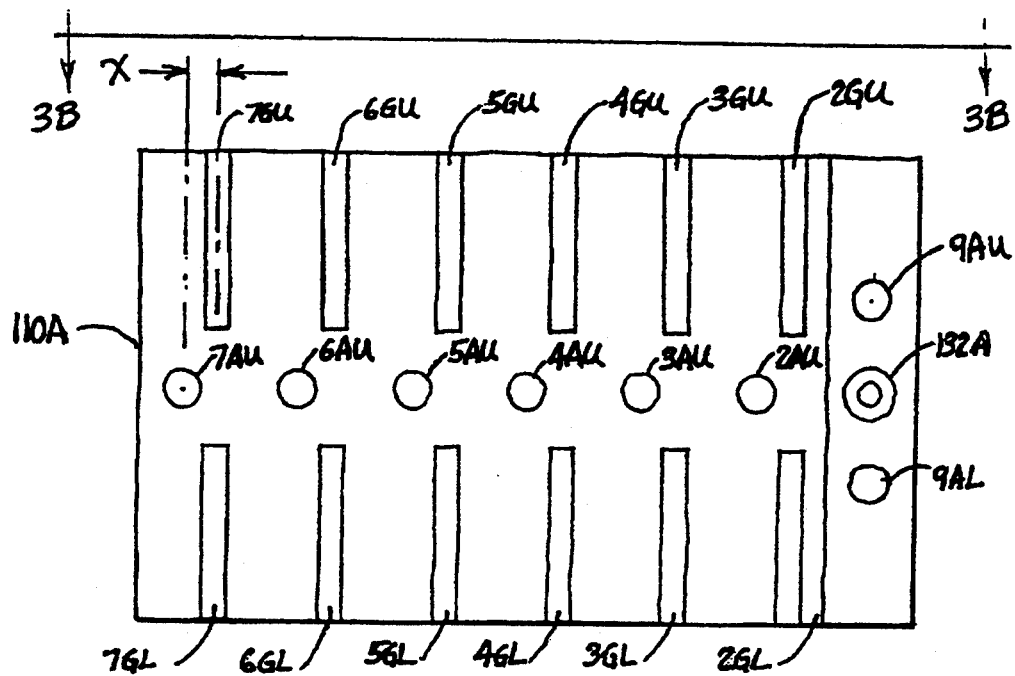
FIG. 3A is front view of block 110A of FIG. 1 shown with connecting member 130A and tower 110A removed.
Figure 3B:
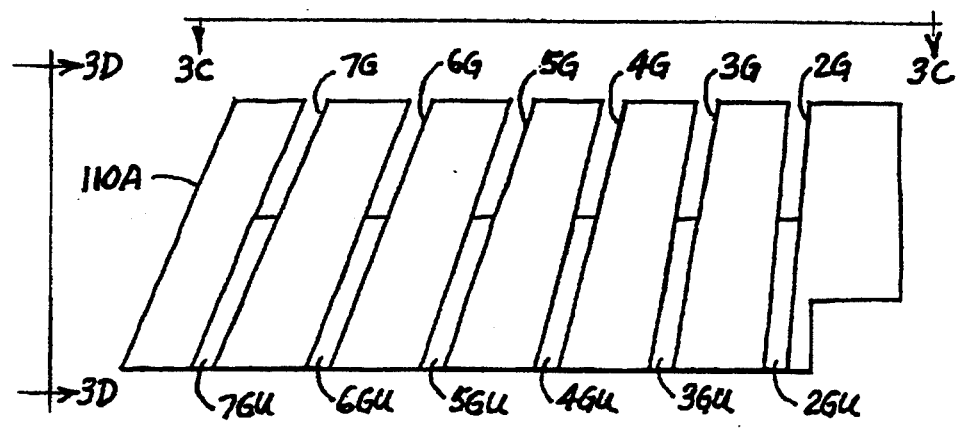
FIG. 3B is a top view of block 110A taken along line 3B—3B of FIG. 3A.
Figure 3C:
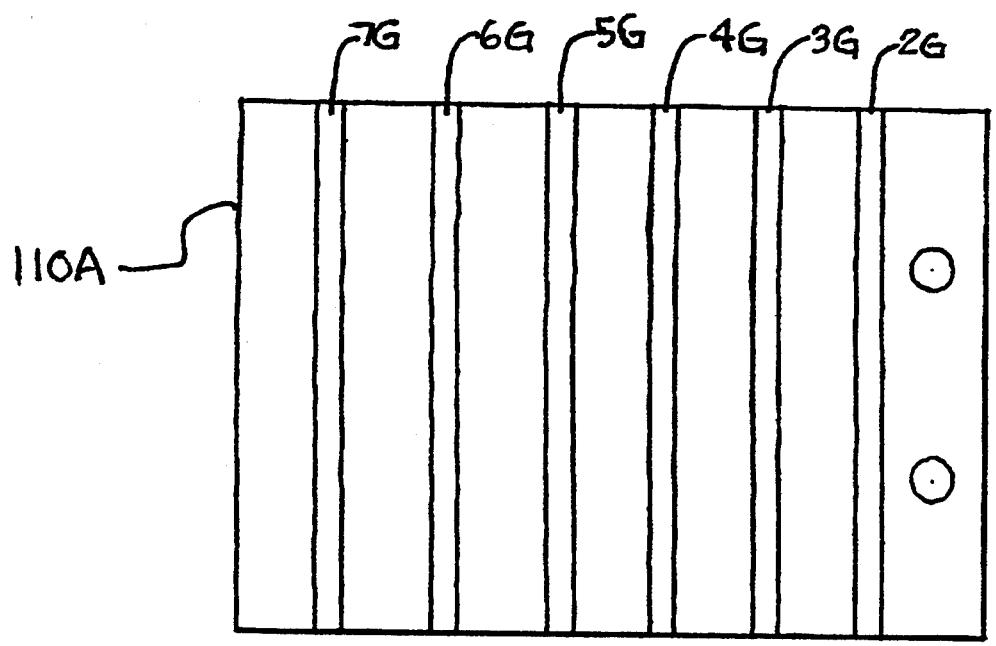
FIG. 3C is a back view of block 110A taken along line 3C—3C of FIG. 3B.

In the preferred embodiment (see FIG. 1) the subject invention comprises a substantially trapezoidal shaped block 110A. The distal end 112A of the block 110A is recessed to receive a L-shaped connecting member 130A. The distal end 112A has two transverse bores 9AU and 9AL extending therethrough (see FIG. 3A). The two bores 9AU and 9AL lie in the same vertical plane, which is perpendicular to the length of the block 110A. The subscript U indicates the upper bore and the subscript L indicates the lower bore. The distal end 112A also has a threaded hole 114A for receiving a connecting pin 132A (see FIG. 4). Disposed in a horizontal plane are a plurality of oblique bores, 2AU,3AU,-4AU,5AU,6AU and 7AU. The L-shaped connecting member 130A (see FIG. 3E) has transverse bores 8AU and 8AL. When connecting member 130A is attached to block 110A, transverse bores 8AU and 8AL align with bores 9AU and 9AL in block 110A. As shown in FIGS. 3A-3C, a plurality of guide slots are disposed in a plurality of vertical planes each parallel to vertical planes through each of the center axes of the oblique bores 2AU-7AU. Each guide slot has an upper portion (for example, 7GU), a lower portion (for example, 7GL) and a connecting portion (for example, 7G) which joins the upper and lower portions across the back side of block 110A (see FIG. 3C).

Figure 3D:
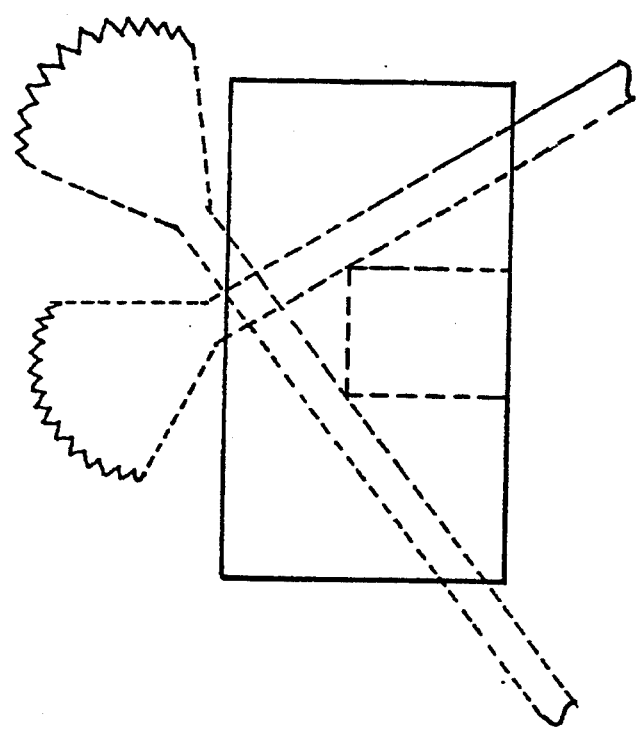
FIG. 3D is a end view of block 110A taken along line 3D—3D of FIG. 3B illustrating saw blade access from above and below.

This interconnection of the upper and lower portions of the guide slot with a connecting portion which forms a continuous slot in the same plane is a key feature of the present invention since it allows the surgeon better access to the bone area of the surgical site. As shown in FIG. 3D, the oscillating saw blade can be inserted in the chosen guide slot from either above or below block 110A. Thus the surgeon can choose whichever aspect best suits each stage of the surgery and can thereby remove the required bone wedge more efficiently and with less trauma to the patient.

The plurality of guide slots are positioned so that the proximal interior face of each guide slot is displaced a horizontal distance X from the vertical plane through the center axis of its corresponding bore (see FIG. 3A). The bore-guide slot pair 2AU-2G is angled 7½ degrees from a vertical plane passing through the centers of transverse bores 9AU-9AL. Each succeeding bore-guide slot pair 3AU-3G, 4AU-4G, etc. is displaced an additional 2½ degrees from the preceding bore-guide slot pair. For example, the pair 3AU-3G are angled 2½ degrees from the bores 2AU-2G and 9½ degrees from the bores 1U-1G. Each of these bores has the same diameter which is selected to tightly receive one of the surgical pins 120A. Guide slots 1G-7G are adapted so that any one can hold and guide an osteotomy saw. The size of each guide slot 1G-7G and the horizontal dispacement distance X are chosen to suit the particular requirements of the osteotomy saw appropriate for the surgical procedure.

Figure 2:
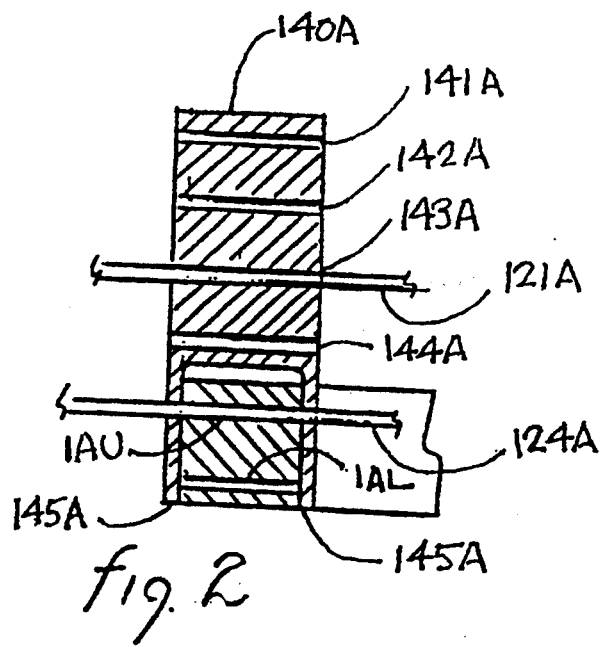
FIG. 2 is a cross-sectional view taken along line 2—2 of FIG. 1.
Figures 3E, 3F:
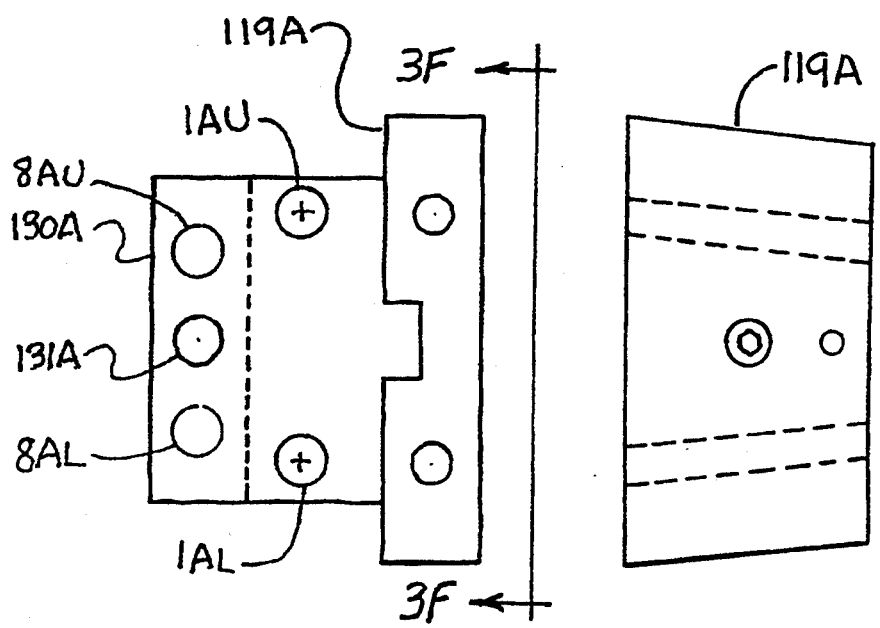
FIG. 3E is a top view of a side plate 119A used for attaching screws.
FIG. 3F is a side view of the side plate 119A taken along line 3F—3F of FIG. 3E.
Figure 8:
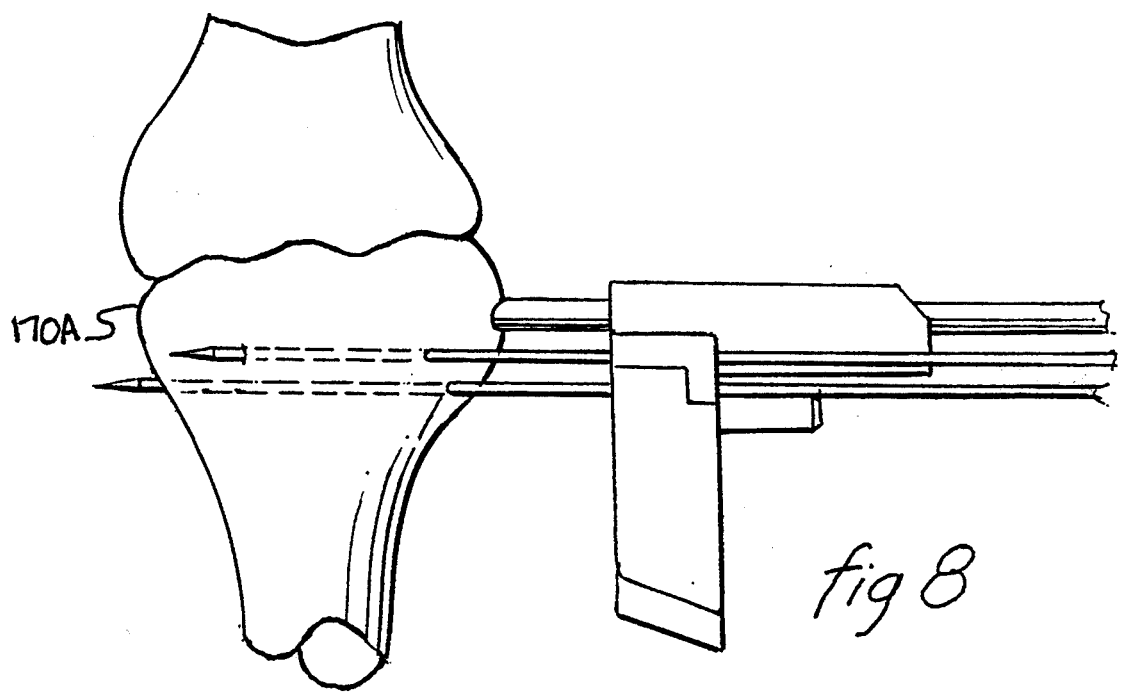
FIG. 8 is a perspective view with the top tower of the osteotomy device of FIG. 7 removed and the lower transverse pins drilled into the bone.
Figure 9:
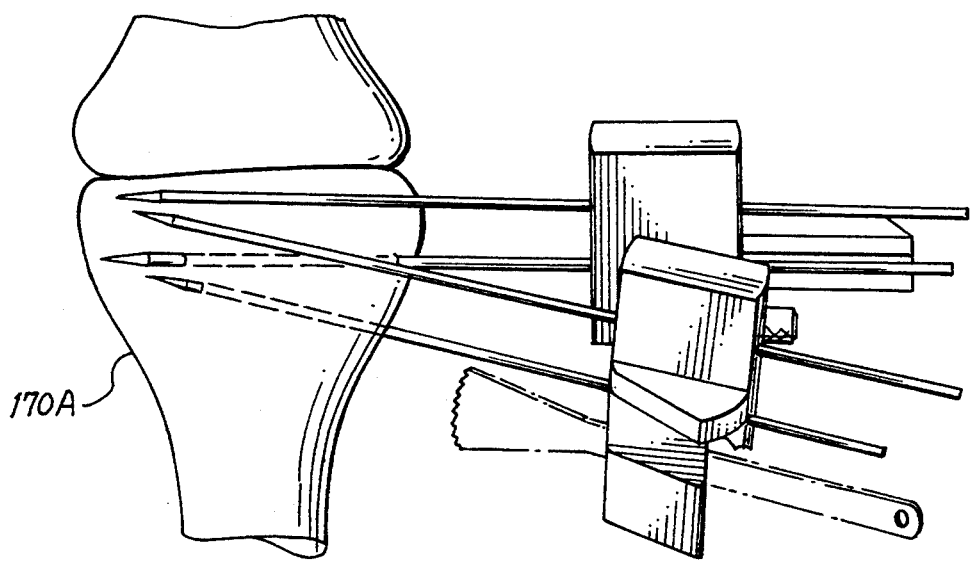
FIG. 9 is a perspective view of the osteotomy device of FIGS. 7 and 8 with an external oblique pin aligned at a predefined angle with the transverse pin.
Figure 10:
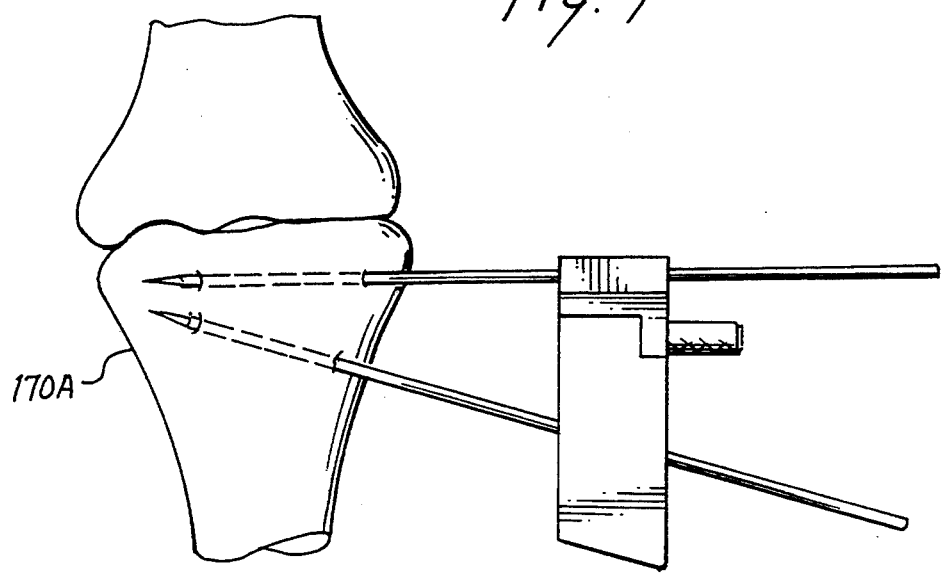
FIG. 10 shows the lower oblique and transverse pins guided by the osteotomy device and drilled in place in the leg bone after the procedure of FIG. 9.
Figure 11:
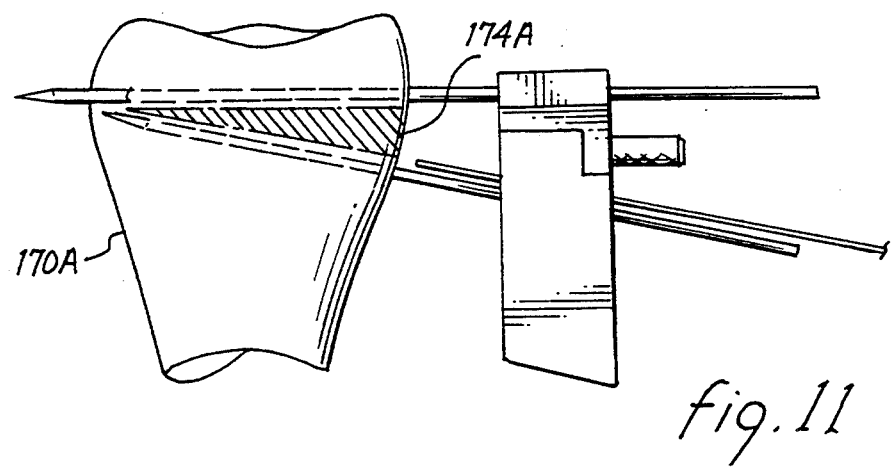
FIG. 11 is a view similar to FIG. 10 with a portion representing the bone wedge to be removed shown in cross-section.

The L-shaped connecting member 130A, (see FIG. 3A and FIG. 4), also has a hole 131A for receiving the connecting pin 132A and two transverse bores 8AU, SAL. The connecting member 130A is sized and shaped so that when it is attached to the distal end 112A of the block 110A by inserting the connecting pin 132A through hole 131A and hole 114A, the bores 8AU, SAL align with the bores 9AU,9AL respectively. Connecting member 130A is adapted to couple to a guide which is designed to be perpendicular to block 110A and which can therefore facilitate the transverse bone cut at the surgical site. The guide can take a variety of forms which are standard equipment for osteotomy procedures such as a guide for a saw, a bone chisel or a drill. FIG. 1 and FIG. 2 show the use of a cutting guide 118A for a bone chisel. FIG. 3E and FIG. 3F show the use of a side plate 119A used for attaching screws (not shown). The two part design combining the connecting member 130A to the distal end 112A by the connecting pin 132A allows for fast and easy removal of the guide 118A from the block 110A after the surgical pins 120A have been inserted into the bone without disturbing the position of the inserted surgical pins 120A.

A first rectangular tower 140A, (see FIG. 2), has four transverse bores 141A,142A,142A and 144A extending therethrough. Each of the bores 141A,142A,142A and 114A are sized to receive one of the surgical pins 120A and lie in the same vertical plane but at different heights. Extending downward from the bottom of the tower 140A are two legs 145A. The distance between the two legs 145A is selected to allow the two legs 145A to slip fit over the distal end 112A and connecting member 130A after the connecting member 130A has been attached to the block 110A. Each of the legs 145A has a slit 146A to assure that the legs 145A do not block the traverse bores 1AU and 1AL.

A second rectangular tower 150A, (see FIG. 1), has four transverse bores 151A,152A,153A and 154A extending therethrough. Each of the bores 151A,152A,153A and 154A are sized to receive one of the surgical pins 120A and lie in the same vertical plane but at different heights. The tower 150A has an integral ovate base 156A with a prong 166A which is sized to be inserted into any of the bores 2AU–7AU to properly establish the position of tower 150A.

The surgical pins 120A are all of identical length. Each of the pins 120A has a pointed end and is strong enough to be drilled into bone without bending. Four surgical pins 120A are required when using the subject invention. For illustrative purposes only the following surgical pins 120A are identified in the drawings and in the following description as follows. Surgical pin 121A is inserted through the bore 142A in the tower 140A. Surgical pin 122A is inserted through the bore 153A in the tower 150A. Surgical pin 124A is inserted through the bore 1AU. Surgical pin 125A is inserted through the bore 6AU.

Each of the components of the subject invention is preferably made of metal and can be sterilized.

In the preferred embodiment of FIG. 1, the subject invention would operate as follows. Starting from the point where all of the components are disassembled, first, the distal end 112A of the block 110A is coupled to the connecting member 130A by inserting the connecting pin 132A through the holes 114A and 131A. The guide 118A is then attached to the connecting member 130A. This combination of components is positioned adjacent to the subject bone 170A which is illustrated in skeletal form in the drawings (see FIGS. 5–11). The combination is adjusted until the block 110A is parallel to the bone 170A. The tower 140A is then slip fit over the distal end 112A and connecting member 130A so that the bores 141A–144A lie in a vertical plane parallel to vertical planes through the longitudinal axes of bores 1AU and 1AL. The surgical pin 121A is inserted through the bore 143A. The selection of the bore 143A is for illustrative purposes only. In actual operation the choice of which bore to use is determined by the thickness of the soft tissue of the leg. The bore that allows the surgical pin 121A to pass closest to the leg without touching the leg is preferably selected. The surgical pin 121A is inserted through the bore 143A until the surgeon estimates that the tip of the pin 121A is directly above the apex 172A of the bone wedge 174A. The position of the pin 121A relative to the apex 172A is then checked by X-rays and any adjustments are made as needed to the position of the pin 121A. The surgeon then slides the surgical pin 124A through the bores 1AU and drills surgical pin 124A into the leg until the end of pins 124A aligns with the end of the pin 121A. Once this procedure is completed the position of the apex 172A of the bone wedge 174A is established. Also, should the device be accidently moved it can always be accurately realigned by sliding the device along the pin 124A until the ends of the pins 124A and 121A are once again aligned.

As one skilled in the art would know, the angle of the bone wedge is substantially equal to the angle through which the leg must be rotated to realign the lower leg. Assuming this angle is seventeen and one-half degrees, the surgeon then inserts the prong 166A into bore 6AU. A bore in tower 150A is selected to be at approximately the same height as the pin previously inserted in a bore of tower 140A. For the particular case of FIG. 1, it is assumed that bore 153A lies at the same height as the bore 153A. The surgical pin 122A is inserted through the bore 153A until the tip of the pin 122A meets the tip of the pin 121A. Once this position has been established, tower 150A is removed. The surgical pin 125A is then inserted through the bore 6AU and drilled into the bone 170A until the end of the pin 125A aligns with the end of the pin 124A. The tower 140A along with the pin 121A is also removed. Block 110A and connecting member 130A are now securely positioned with respect to bone 170A by surgical pin 124A which has been drilled into bone 170A through transverse bore 1U and by surgical pin 125A which has been drilled into bone 170A through oblique bore 6AU. The surgeon now attaches an appropriate cutting guide onto connecting member 130A and uses it to guide the making of a first transverse cut into bone 170A thereby forming one face of the bone wedge 174A which is to be removed. The surgeon next inserts a suitable osteotomy saw into guide slot 6G and makes a second oblique cut into bone 170A thereby forming the second face of bone wedge 174A. The particular configuration of the guide slot with its upper portion 6GU, its lower portion 6GL and the connecting portion 6G are a key advantage of the present invention since they allow the surgeon to apply the osteotomy saw to bone 170A from a position either above or below block 110A, thereby allowing bone wedge 174A to be removed it the most expeditious manner. Because of the particular arrangement of the bores, pins and guide slots of the subject invention, the saw cuts which form bone wedge 174A will intersect at precisely the required apex position 172A which will provide the optimum surgical result. After bone wedge 174A has been removed, the connecting pin 132A is unscrewed and the connecting member 130A along with the guide 118A is removed by sliding the connecting backward over the pin 124A. The block 110A is then removed by sliding it backwards over the pin 125A. Pins 124A and 125A are then removed and the remainder of the surgical procedure is completed.

The osteotomy device which has been described for the preferred embodiment can be rotated so that they can be used on both left and right legs.

While the invention has been particularly shown and described with reference to a preferred embodiment thereof, it will be understood by those skilled in the art that changes in form and detail may be made therein without departing form the spirit and the scope of the invention. External locator means, as defined herein, comprise both the first tower member which contains a plurality of transverse bores sized to receive a number of surgical pins that extend therethrough and the second tower member which contains a plurality of transverse bores sized to receive a number of the surgical pins that extend therethrough. The internal locator means comprise the surgical pins that are inserted through the transverse and oblique bores.

I claim:

1. An osteotomy guide used in the removal of a wedge shaped piece of bone from patient's leg, which comprises:
   a plurality of surgical pins;
   a block having a top side, a bottom side and a back side and having a first transverse bore extending therethrough, a transverse guide slot extending therethrough, a plurality of oblique bores extending therethrough, and a plurality of oblique guide slots extending therethrough, said first transverse bore and said transverse guide slot being orthogonal with said back side and said oblique bores being aligned with said transverse bore in a horizontal plane and said oblique bores and oblique guide slots being positioned at predetermined angles from said transverse bore and transverse guide slot, said transverse and oblique bores being sized to receive said surgical pins and said transverse and oblique guide slots being sized to receive an osteotomy saw, said oblique guide slots comprising an upper portion in said top side, a lower portion in said bottom side and a connecting portion in said back side;
   a first tower member, disposed atop said block and in line with said first transverse bore, and having a plurality of transverse bores sized to receive a number of said surgical pins for extending therethrough; and
   a second tower member, having a plurality of oblique bores sized to receive a number of said surgical pins for extending therethrough disposed atop said block and coupled to one of said oblique bores so that said transverse bores of said second tower are aligned at the same predetermined angle as said oblique bore coupled thereto.

2. The device recited in claim 1 wherein said second tower member has an integral ovate base, said base having a prong extending therefrom for insertion into any of said oblique bores.

3. The device recited in claim 1 further comprising:
   a bone cutting member; and
   means for coupling said bone cutting member to said block so that said bone cutting member is positioned perpendicular to said back face of said block.

4. The device recited in claim 3 wherein said means for coupling is an L-shaped member screwably coupled to said bone cutting member and to said block.

5. The device recited in claim 3 wherein said bone cutting member is a seating chisel.

6. The device recited in claim 3 wherein said means for coupling is a side plate for guiding a bone drill.

7. The device recited in claim 3 wherein said bone cutting member is a bone drill used for attaching screws.

8. The device recited in claim 1 wherein said first tower member has a pair of legs extending downwardly over said block.

9. The device recited in claim 8 wherein each of said legs has a slit extending from the bottom of each of said legs to a level which allows access to said first transverse bore.

10. An osteotomy guide used in the removal of a wedge shaped piece of bone from a patient's leg, said piece of bone having first and second sides that intersect at the apex of the wedge, the angle between said first and second sides being substantially equal to the angle through which said leg must be rotated to correct the leg's misalignment, which comprises:
    block means for establishing a reference position adjacent to the patient's leg;
    first locator means coupled to said block means for establishing the positions of said apex and said first and second sides of said bone wedge externally above the patient's leg; and
    second locator means coupled to said block means for establishing said positions, from said first locator means, inside the patient's leg; said block means transmitting said positions determined by said first locator means to said second locator means, said first locator means disposed atop said block means, and said second locator means being integral with said block means, said block means further comprising guide means for aligning a bone cutting device with said positions established by said second locator means, said guide means further comprising means for applying said bone cutting device from both an upper and a lower access point with respect to the leg bone in the patient's leg, further comprising a plurality of surgical pins for use in bores in said first locator means, said block means further comprises a block having a top side, a bottom side and a back side and having a first transverse bore extending therethrough, a transverse guide slot extending therethrough, a plurality of oblique bores extending therethrough, and a plurality of oblique guide slots extending therethrough, said first transverse bore and said transverse guide slot being orthogonal with said back side and said oblique bores being aligned with said transverse bore in a horizontal plane and said oblique bores and oblique guide slots being positioned at predetermined angles from said transverse bore and transverse guide slot, said transverse and oblique bores being sized to receive said surgical pins and said transverse and oblique guide slots being sized to receive an osteotomy saw, said transverse and oblique guide slots comprising an upper portion in said top side, a lower portion in said bottom side and a connecting portion in said back side.

11. The device recited in claim 10 wherein said external locator means is further comprised of:
    a first tower member having a plurality of transverse bores sized to receive a number of said surgical pins for extending therethrough; and
    a second tower member having a plurality of transverse bores sized to receive a number of said surgical pins for extending therethrough coupled to one of said oblique bores so that said transverse bores of said second tower are aligned at the same predetermined angle as said oblique bores coupled thereto.

12. The device recited in claim 11 wherein said second locator means is further comprised of said surgical pins inserted through said transverse and oblique bores.

13. A method for removing a bone wedge from a leg bone, comprising the steps of:
    providing a plurality of surgical pins;
    providing a substantially trapezoidal shaped block having a first bore-guide slot pair extending therethrough and a plurality of oblique bore-guide slot pairs extending therethrough, wherein the longitudinal axes of the oblique bores of said oblique bore-guide slot pairs are positioned at predetermined angles from the longitudinal axis of the first bore of said first bore-guide slot pair, said oblique bores being aligned with said first transverse bore in a horizontal plane, wherein said transverse and oblique bores are sized to receive said surgical pins, and the guide slots of said bore-guide slot pairs are sized to receive a surgical saw said transverse and oblique guide slots comprising an upper portion in said top side, a lower portion in said bottom side and a connecting portion in said back side;

positioning said block parallel with the leg bone;

providing a first tower member having a plurality of transverse bores sized to receive said surgical pins for extending therethrough;

mounting said first tower atop said block so that said transverse bores in said first tower are aligned with said first transverse bore;

providing a second tower member having a plurality of transverse bores sized to receive said surgical pins for extending therethrough;

selecting said predetermined angle and selecting said oblique bores at said predetermined angle;

coupling said second tower to one of said selected oblique bores;

adjusting the height of said second tower so that said transverse bores of said second tower are at the same height as said transverse bores of said first tower;

inserting one of said surgical pins through one of said transverse bores of said first tower until the tip of said surgical pin is positioned above the apex of said bone wedge;

inserting one of said surgical pins through the bore of said first transverse bore-guide slot pair and into the leg bone until the end of said surgical pin aligns with the end of said surgical pin inserted through said first tower;

inserting one of said surgical pins through one of said transverse bores of said second tower at the same height as said transverse bore used in said first tower;

adjusting the position of the tip of said surgical pin inserted through said first tower until said tip abuts the tip of said surgical pin inserted through said second tower;

inserting one of said surgical pins through the bore of one of said oblique bore-guide slot pairs positioned at said selected angle and into the leg bone until the end of said surgical pin aligns with the end of said surgical pin inserted through said second tower;

removing said second tower along with said surgical pin inserted therein;

removing said first tower and said block;

attaching a cutting guide to the distal end of said block; and guiding a surgical saw with said cutting guide to make a transverse cut into the leg bone and inserting said surgical saw into the selected oblique guide slot to perform a cutting operation to cut out a right angled wedge shaped portion from the leg bone.

14. An osteotomy device used in the removal of a wedge shaped piece of bone from a patient's leg bone, comprising:

block means for establishing a device structure parallel to said patient's leg bone;

connecting means detachably coupled to said block means for extending the distal end of said device structure;

first tower means detachably coupled to said connecting means for temporarily extending said device structure;

first locating pin means coupled to said first tower means for locating external to the leg of said patient the position of a first face of said wedge shaped piece of bone;

first pin means coupled to said connecting means for drilling into said patient's leg bone along an axis parallel to the longitudinal axis of said first locating pin means first guide slot means coupled to said connecting means for guiding an osteotomy saw in cutting said first face of said wedge shaped piece of bone;

second tower means detachably coupled to said block means for temporarily extending said device structure;

second locating pin means coupled to said second tower means for locating external to the leg of said patient the position of a second face of said wedge shaped piece of bone;

second pin means coupled to said connecting means for drilling into said patient's leg bone along an axis parallel to the longitudinal axis of said second locating pin means second guide slot means coupled to said connecting means for guiding an osteotomy saw in cutting said second face of said wedge shaped piece of bone, said second guide slot means further comprising means for accessing a bone cutting device from positions both above and below the longitudinal axis of said leg bone.

* * * * *